United States Patent
Ashkenazi (10) Patent No.: US 10,925,528 B2
(45) Date of Patent: Feb. 23, 2021

(54) DEPTH SCANNING OXYGEN SENSOR

(71) Applicant: A-SCAN LLC, St. Louis Park, MN (US)

(72) Inventor: Shai Ashkenazi, St. Louis Park, MN (US)

(73) Assignee: A-SCAN LLC, St. Louis Park, MN (US)

( * ) Notice: Subject to any disclaimer, the term of this patent is extended or adjusted under 35 U.S.C. 154(b) by 312 days.

(21) Appl. No.: 15/763,283

(22) PCT Filed: Oct. 17, 2016

(86) PCT No.: PCT/US2016/057326
§ 371 (c)(1),
(2) Date: Mar. 26, 2018

(87) PCT Pub. No.: WO2017/070046
PCT Pub. Date: Apr. 27, 2017

(65) Prior Publication Data
US 2018/0271411 A1   Sep. 27, 2018

Related U.S. Application Data

(60) Provisional application No. 62/244,404, filed on Oct. 21, 2015.

(51) Int. Cl.
*A61B 5/1455* (2006.01)
*A61B 5/1459* (2006.01)
(Continued)

(52) U.S. Cl.
CPC .............. *A61B 5/1459* (2013.01); *A61B 5/01* (2013.01); *A61B 5/14539* (2013.01);
(Continued)

(58) Field of Classification Search
None
See application file for complete search history.

(56) References Cited

U.S. PATENT DOCUMENTS 4,476,870 A   10/1984   Peterson et al.
4,582,064 A   4/1986   Sorger
(Continued)

FOREIGN PATENT DOCUMENTS

WO   2014/195363 A1   12/2014

OTHER PUBLICATIONS

Oxygen in Human Tumors: Correlations between Methods of Measurement and Response to Therapy: Summary of a Workshop Held Nov. 19-20, 1992, at the National Cancer Institute, Bethesda, Maryland; Authors: Helen B. Stone, J Martin Brown, Theodore L. Phillips and Robert M Sutherland; Source: Radiation Research, vol. 136, No. 3 (Dec. 1993), pp. 422-434.

(Continued)

*Primary Examiner* — Marjan Fardanesh
(74) *Attorney, Agent, or Firm* — Vidas, Arrett & Steinkraus, P.A.

(57) ABSTRACT

An oxygen scanning device includes a console unit. The console unit includes a light source emitting excitation radiation and a detector configured to receive and detect phosphorescence radiation. The device includes a needle sensor operably, optically coupled to the console unit by an optical fiber movably received within a transparent tube housing the optical fiber, the transparent tube being coated by an oxygen-sensitive dye material on an outer side thereof. The optical fiber is terminated by a 45 degree reflecting surface at a distal end thereof wherein excitation radiation is directed to the oxygen sensitive dye material and phosphorescence radiation from the oxygen sensitive material is returned from the oxygen sensitive material to the detector.

13 Claims, 3 Drawing Sheets

(51) Int. Cl.

| | |
|---|---|
| *A61B 5/145* | (2006.01) |
| *G01N 21/77* | (2006.01) |
| *A61B 5/1473* | (2006.01) |
| *G01N 31/22* | (2006.01) |
| *A61B 5/01* | (2006.01) |
| *A61B 5/00* | (2006.01) |

(52) U.S. Cl.
CPC ...... *A61B 5/14556* (2013.01); *A61B 5/14735* (2013.01); *A61B 5/6848* (2013.01); *G01N 21/77* (2013.01); *G01N 31/22* (2013.01); *A61B 5/0071* (2013.01); *G01N 2021/7709* (2013.01); *G01N 2021/7786* (2013.01); *G01N 2021/7796* (2013.01)

(56) References Cited

U.S. PATENT DOCUMENTS

| | | | |
|---|---|---|---|
| 4,752,115 | A | 6/1988 | Murray, Jr. et al. |
| 6,274,086 | B1 | 8/2001 | Wilson et al. |
| 8,554,297 | B2 | 10/2013 | Moon et al. |
| 2005/0113658 | A1 | 5/2005 | Jacobson et al. |
| 2008/0199360 | A1 | 8/2008 | Shahriari |
| 2009/0216097 | A1 | 8/2009 | Wilson et al. |
| 2010/0249558 | A1 | 9/2010 | Yodfat et al. |
| 2011/0105869 | A1 | 5/2011 | Wilson et al. |
| 2011/0184259 | A1 | 7/2011 | Alarcon et al. |
| 2015/0190080 | A1 | 7/2015 | Ashkenazi |

OTHER PUBLICATIONS

O. Stern and M Volmer; Physikalische Zeitschrift 20, p. 183-8, (1919).
S.M. Grist, L. Chrostowski, and K. C. Cheung. "Optical oxygen sensors for applications in microjluidic cell culture." Sensors 10.10: p. 9286-9316 (2010).
P.Vaupel, M Hackel, and A. Mayer; "Detection and Characterization of Tumor Hypoxia Using pO 2 Histography" Antioxidants & Redox Signaling, vol. 9, No. 8, (2007).
D. De Backer, K. Donadello, and D. Orbegozo Cortes; "Monitoring the microcirculation", J Clin Manit Comput 26, p. 361-366 (2012).
C. Xue, A. Friedman, and C. K. Sen; "A mathematical model of ischemic cutaneous wounds"; Proceedings of the National Academy of Sciences of the United States of America. 106(39), p. 16782-16787 (2009).
D. Ross, M Gaitan, and L. E. Locascio; "Temperature Measurement in Microjluidic Systems Using a Temperature-Dependent Fluorescent Dye"; Anal. Chem., 73, 4117-4123 (2001).
H. Boaz and G. K. Rollefson, "The Quenching of Fluorescence. Deviations from the Stern-Volmer Law," JAm. Chem. Soc. 72(8), p. 3435-3443 (1950).
L. M Coyle, and M Gouterman, "Correcting lifetime measurements for temperature", Sensors and Actuators B 61, p. 92-99 (1999).
B. Zelelow, G. E. Khalil, G. Phelan, B. Carlson, M Gouterman, J B. Callis, and L R. Dalton "Dual luminophor pressure sensitive paint: II Lifetime based measurement of pressure and temperature." Sensors and Actuators B: Chemical 96.1, p. 304-314 (2003).

DEPTH SCANNING OXYGEN SENSOR

FIELD OF THE INVENTION

The invention relates to target substance sensors for medical applications and other applications. More particularly the invention relates to sensing oxygen and other target substances as a function of tissue depth.

BACKGROUND OF THE INVENTION

Oxygen plays a critical role in tissue viability and function in almost all living forms and particularly in mammalians. It is essential for cellular metabolism and proliferation. In humans (and other mammals) oxygen is absorbed form air in the lungs and reversibly binds to hemoglobin in red blood cells. It is then transported by blood circulation to all parts of the body. Capillaries in the vasculature system function as oxygen exchangers enabling oxygen transfer with the tissue. This allows oxygen to be delivered into cells by diffusion through the tissue. The distance between any specific cell and the capillary net surrounding it is typically around 100 μm. Cells use up oxygen in the process of aerobic production of ATP (adenosine triphosphate, an energy intermediate molecular agent) in a process referred to as cellular respiration. The supply of oxygen by diffusion transport is balanced inside cells by oxygen consumption. Different factors can alter the local partial pressure of oxygen (pO2) and its distribution. These factors include: the rate of cellular respiration, distance from capillaries, damaged capillaries, tissue type, and tissue function. Variability in these parameters leads to inhomogeneous distribution of pO2 in the body. Measuring pO2 distribution can thus provide valuable information that is useful for disease diagnosis and treatment planning.

Beyond its role in metabolism, oxygen is involved in several other physiological processes. It has a prime role in regulating cancer growth, mainly through the production of Hypoxia inducible factor 1 (HIF1). Many cancer tumors show a characteristic structure of a highly hypoxic core surrounded by hypermetabolic malignant cancer cells.

Different forms of cancer therapy such as radiation therapy and photodynamic therapy rely on sufficient level of pO2 in the tissue treated and their efficacy is highly correlated with tissue oxygen level.

The process of tissue repair in wound healing is also highly dependent on the availability of oxygen in the tissue. Methods of enhancing tissue oxygenation in patients with difficult to heal wounds are commonly used to improve treatment. In these cases, it is essential to resolve the distribution of pO2 within the wound and tissue surrounding the wound in order to monitor the efficacy of treatments.

Although the significance of obtaining information on pO2 distribution in the body is widely acknowledged in the scientific and medical research community, it has not been translated to clinical methods to improve patient treatment in a clinical setting. The main reason is a lack of medical devices that can be successfully applied in clinical environment.

Some prior art devices rely on measurement of oxygen saturation. Oxygen saturation is the ratio of oxy-hemoglobin to total hemoglobin concentration. Oxygen saturation measurement devices generally rely on changes in hemoglobin light absorption induced by binding to oxygen. It is an indirect way to assess tissue oxygen in a relatively large volume of tissue. U.S. Pat. No. 8,554,297 B2 describes a pulse oximeter device that is based on absorption spectral measurements of tissue at two wavelengths of light. Tissue oxygen partial pressure is affected by multiple parameters. Hemoglobin saturation is only one of them. Accordingly, there is no reliable way to use this sort of device to extract tissue oxygen information.

Direct measurement of tissue oxygen can be conducted by the use of polarographic oxygen electrodes (ref: "*Oxygen in Human Tumors: Correlations between Methods of Measurement and Response to Therapy: Summary of a Workshop Held Nov. 19-20, 1992, at the National Cancer Institute, Bethesda, Md.*"; Authors: Helen B. Stone, J. Martin Brown, Theodore L. Phillips and Robert M. Sutherland; Source: *Radiation Research*, Vol. 136, No. 3 (December, 1993), pp. 422-434). These devices rely on electrochemical response of a metal electrode to changes in pO2. An electrode embedded in a needle is used to measure tissue oxygen at the tip of the needle. The needle can be retracted after insertion into the tissue such that the tip is positioned at multiple locations along the insertion axis to resolve depth related distribution of tissue oxygen. An example of a design of such a device is described in ref U.S. Pat. No. 4,582,064 A. Although this device directly measures tissue oxygen it has several drawbacks that are inherent to this technology. First, polarographic electrodes consume a small amount of oxygen during operation. This prevents their use in monitoring oxygen at one point location for a prolonged time and results in low precision in measuring low levels of oxygen. Second, repeating a measurement requires re-insertion of the needle which results in tissue damage that alters oxygen level in the tissue.

Optical phosphorescence sensing has emerged as an alternative oxygen sensing technology to polarographic electrodes. Phosphorescence emission of many types of dyes is effectively quenched by oxygen. The rate of phosphorescence quenching is linearly dependent on oxygen concentration (ref: O. Stern and M. Volmer; *Physikalische Zeitschrift* 20, p. 183-8, (1919)). Measuring the rate of quenching provides a direct way to measure local concentration of oxygen.

The photophysics of the oxygen quenching process can be described as follows. A dye molecule is excited by absorbing a photon which leads to a change in the electron state of the dye from a ground state to a higher energy singlet state. The higher energy state can relax back to the ground state by emitting a fluorescence photon or by thermal energy transfer to molecular degrees of freedom. The higher energy state can also switch from the singlet state into a triplet state, a process known as intersystem crossing. A triplet state has a much longer lifetime than a singlet state. The lifetime can vary from tens of nanoseconds to minutes depending on the dye as compared to singlet state lifetime which is, in general, less than 10 nanoseconds. The triplet state eventually relaxes back to ground state by emitting a phosphorescence photon. In the presence of oxygen, energy transfer to oxygen through collisions competes with phosphorescence emission. The total rate of decay of the triplet state is the sum of the internal phosphorescence decay rate and the oxygen quenching rate. This mechanism forms the basis for utilizing dye phosphorescence to measure oxygen concentration. A good oxygen-sensitive dye has a high yield of intersystem crossing and a long triplet state lifetime. Longer lifetime provides higher precision in measuring low concentrations of oxygen. However, longer lifetime also result in low emission intensity which can lead to higher noise level in the optical detector which in turn will reduce sensitivity because of reduction in the signal to noise ratio (SNR). Several dyes have been shown to provide good oxygen sensitivity in the physiological range and can be used successfully as oxygen sensors. A compilation of dye properties for a selection of oxygen sensitive dyes can be found in S. M. Grist, L. Chrostowski, and K. C. Cheung. "*Optical oxygen sensors for applications in microfluidic cell culture.*" *Sensors* 10.10: p. 9286-9316 (2010). A partial list of dyes that have been successfully implemented in oxygen probes include: ruthenium-tris-4,7-diphenyl-1,10-phenanthroline ([Ru(dpp)3]2+), ruthenium (II)-tris(1,10-phenanthroline) ([Ru(phen)3]2+), Platinum (II)-octaethyl-porphyrin (PtOEP), palladium(II)-octaethyl-porphyrin (PdOEP), Platinum(II)-octaethyl-porphyrin ketone (PtOEPK), and ruthenium tris(2,2'-dipyridyl) dichloride hexahydrate (RTDP). This list should not be considered limiting.

To form an oxygen sensitive surface, dyes are incorporated in polymer matrix. The polymer can be applied to form a film that can be attached to a solid surface. It also improves phosphorescence by minimizing self-quenching that occurs in dye crystals due to high concentration. The embedding polymer needs to have sufficiently high permeability to gases in order to allow rapid response to changes in oxygen concentration in the environment. Typical materials used in oxygen sensors include but are not limited to: polystyrene, polymethyl methacrylate (PMMA), Cellulose acetate butyrate (CAB), poly(vinyl chloride) (PVC), and Polydimethylsiloxane (PDMS).

The technology of oxygen sensing by phosphorescence measurement has driven the design of a range of devices for measuring tissue oxygen in research settings. U.S. Pat. No. 4,476,870 describes a device in which an excitation optical fiber and a collecting optical fiber are terminated inside a tube filled with a polymer/dye oxygen-sensitive material. The tube is intended to be implanted in tissue or in blood vessel. A needle can be used to deliver the device into the target tissue.

In U.S. Pat. No. 4,752,115 a single-fiber device is described in which the excitation light and the emitted phosphorescence light are delivered through the same optical fiber. In this device tris-(4,7-diphenyl1,10-phenanthroline)-Ru(II) perchlorate is used as an oxygen-sensitive dye. The dye is embedded in a PVC matrix.

In both patents (U.S. Pat. Nos. 4,476,870, 4,752,115) a device is made of bare optical fibers that are exposed to the environment where oxygen is to be measured. In the case of biological tissue there are forces and stresses applied on the device by the surrounding tissue that are likely to damage the device. These devices are, therefore, intended for deposition inside a catheter or a major blood vessel. In such cases the catheter or vessel walls provide mechanical protection and support stable operation. However, this approach can only provide information on oxygen pO2 in the blood within the lumen which can be significantly different than that of the tissue due to the fast convective transport of oxygen in blood. Moreover, the measurement locality is limited to relatively large blood vessels only.

In US 20090216097A1 and US 20110105869A1, the inventors describe improved configurations that are suitable for measuring tissue oxygen while maintaining mechanical stability and withstanding tissue pressures. The configuration includes a measurement chamber composed of a tube made of oxygen permeable material that encloses an oxygen-sensitive dye solution and optical fibers. The tube is sealed at both ends. In the preferred (and experimented) embodiment the tube is made of Teflon® AF material. Optical fibers penetrate through the back seal of the measurement chamber. The optical fibers are used to deliver excitation light and collect emission light. The length of the measurement chamber is several millimeters. This length determines an effective measurement volume where oxygen level is averaged to yield a single mean pO2 value. This averaging volume is said to have a linear side size of 3 to 5 mm in the '869 application.

Although the device disclosed in application '869 seeks to address the issue of mechanical stability under in vivo measurement conditions, the large measurement volume severely limits the range of applications where clinically valuable information can be extracted and used to improve treatment of disease or injuries. Clinical research emphasizes the benefits of resolving tissue oxygen gradients and spatial distribution yet no useful tool to do so is available. For example, Vaupel et. al. in P. Vaupel, M. Hockel, and A. Mayer; "*Detection and Characterization of Tumor Hypoxia Using pO2 Histography*" *ANTIOXIDANTS & REDOX SIGNALING*, Volume 9, Number 8, (2007) have compiled data from 125 research studies analyzing cancer tumor oxygen distribution using an Eppendorf polarographic electrode. Their findings show the importance of resolving the profile of pO2 in a cancer tumors and identifying hypoxic regions.

In considering the field of microcirculation and the effect of microvascular alterations due to disease processes, Backer et. al. in D. De Backer, K. Donadello, and D. Orbegozo Cortes; "*Monitoring the microcirculation*", *J Clin Monit Comput* 26, p. 361-366 (2012) have asserted that "These microvascular alterations are characterized by a decreased capillary density, resulting in increased diffusion distance for oxygen. More importantly, microvascular blood flow is heterogeneous, with perfused capillaries in close vicinity of non perfused capillaries, leading to alterations in oxygen extraction and hypoxic zones even when total blood flow to the organ is preserved". This observation highlights the need for local resolution of tissue pO2.

A particular example of alteration in microcirculation is in the case of wounds. It is well known that sufficient level of oxygen is essential for wound healing. Many diabetes patients suffer from damage to capillaries and loss of microcirculation in localized regions. This condition leads to wounds that are very slow to heal or non-healing wounds that, in severe cases, result in gangrene which often necessitates limb amputation. Resolving local gradients and distribution of oxygen in the wound region can provide valuable information for treating ischemic wounds (see for example C. Xue, A. Friedman, and C. K. Sen; "*A mathematical model of ischemic cutaneous wounds*"; *Proceedings of the National Academy of Sciences of the United States of America.* 106(39), p. 16782-16787 (2009).

Based on the above information, there is room for improvement in the measurement of tissue oxygen levels for a variety of medical circumstances.

SUMMARY OF THE INVENTION

The invention solves many of the above discussed problems of the prior art and provides a tissue oxygen sensor that directly measures pO2 at multiple locations along a linear path inside a tissue. Example embodiments of the invention presented here improve on prior art devices in part because they measure a depth-profile (or any linear profile in any arbitrary direction) of tissue pO2 while no mechanical motion occurs between the tissue and the device. Furthermore, the device is protected and designed to withstand tissue-exerted pressures for continuous operation in a tissue environment.

No oxygen probe known to the inventor delivers all of the following features that support successful implementation in clinical circumstances.
1. Direct measurement of tissue oxygen.
2. Rugged design that can sustain stress exerted on the device by the tissue.
3. Prolonged operation in monitoring for extended period of time (resolving temporal dynamics).
4. Resolving spatial distribution of pO2 without the need to mechanically translate the probe with respect to the tissue.

Example embodiments of the invention are expected to improve diagnoses and thus support better treatment of patients suffering from a range of pathologies and conditions related to tissue viability, microcirculation and oxygen perfusion. Applications of the invention include but are not limited to: monitoring of wound healing, diagnosis of diabetic ulcers, monitoring tissue flap reconstructive surgery and in-line monitoring of tissue during spine surgery. A device according to example embodiments of the invention presents distinct advantages over current technology of needle based oxygen sensors. Expected advantages include:
1. A depth-resolved profile of tissue pO2 that provides the physician with better diagnostic information than a single-point measurement of tissue pO2 as provided by current technology.
2. Embodiments of the invention enable a very small needle diameter (down to 0.25 mm), thereby minimizing damage to blood vessels and reducing patient pain.
3. The small size of an active element according to example embodiments of the invention is expected to facilitate a very short response time (shorter than 1 s).
4. By separating the optical fiber and the oxygen sensitive film, embodiments of the invention allow protection of the optical fiber in a capillary tube. This design provides superior robustness over existing devices in which the sensitive film is coated on a fiber tip. In these latter devices physical forces applied by the tissue are directly transferred to the optical fiber which leads to high rate of mechanically induced damages to the fiber and therefore device failure. The improved design is expected to enable embodiments of the invention to withstand stress which typically results from insertion of a needle into tissue and thus is applicable for the design of medical needle sensor for use in clinical applications.

The console unit includes a light source for dye excitation, light detector for detecting phosphorescence signals, and a fiber coupler for coupling light from the source to the connecting optical fiber and coupling phosphorescence light from the fiber to the detector. A motorized mechanical scanning device is housed in the console unit and supports the optical fiber to cause translation of the connecting optical fiber while maintaining a constant fiber orientation relative to rotation.

The console unit also includes a digital electronic controller (such as a computer). The controller allows the programming of amplitude modulation of the light source in different patterns such as short pulses, square waveforms, and sinusoidal waveforms. The controller also enables acquisition of electronic signals from the phosphorescence light detector as well as digitization, digital signal processing, data display and communication. The controller also controls the motorized fiber scanning device thus enabling positional and orientation control of the fiber tip.

The needle sensor includes a glass capillary coated on its exterior side with an oxygen sensing dye and housed in a stainless steel needle. The needle has a side window that permits physical contact or close apposition between the tissue (or the environment in which the needle is immersed) and the sensing layer. The glass capillary is sealed at its distal end to prevent oxygen transfer from air inside the capillary to the tissue.

The sensing dye is embedded in a polymer matrix and forms a thin layer on the outer wall of the glass capillary. An optical fiber (for example a 105 micrometer core multimode optical fiber having a numerical aperture of 0.22) is angle-polished at an angle greater than the critical angle for total internal reflection in air. This type of fiber termination is used for side illumination. The waveguide is then inserted into the glass capillary which is sealed at its distal end. This example configuration allows for excitation light to be delivered by the optical fiber to illuminate a small area of the sensing layer coated on the outer side of the capillary.

The excitation of the dye in the sensing layer generates phosphorescence emission. Phosphorescence is, in general, a non-directional emission radiation and therefore most of the emitted phosphorescence radiation will be absorbed by the needle structure or propagate into the surrounding tissue. Some part of the emitted light, however, propagates in the direction of the angle-polished tip of the fiber waveguide, couples to the waveguide and propagates back to the remote end of the waveguide located in the console unit.

The efficiency of collecting phosphorescence light through the same waveguide that delivers the excitation light depends on the numerical aperture of the waveguide, its polishing angle, and other geometrical parameters. A large numerical aperture increases the efficiency of collection, however, it also requires a larger angle of waveguide termination in order to maximize the amount of excitation light that undergoes total internal reflection and is directed towards the sensing layer. For example, if the waveguide is an optical fiber of numerical aperture of 0.22, a core diameter of 0.105 mm, and a capillary tube of 0.15 mm inner diameter, and 0.25 mm outer diameter, numerical modeling employing ray tracing approximation predicts efficiency of about 6% and an optimal angle of 45 degrees. Phosphorescence light that is coupled to the fiber is delivered by the fiber back to the console unit for detection. Light focusing can also be used to reduce the illumination spot size on the sensing layer. This can be achieved by means of an additional lens or a curved mirror proximate the end of the optical fiber.

The size and position of the illumination spot on the sensing layer defines the effective sensing area. The location of the effective sensing area is moved along the length of the sensing layer by mechanically scanning the fiber inside the glass capillary. A scanning actuator, facilitating precise fiber movement, is positioned, for example, in the console unit and is controlled by the system's controller.

The phosphorescence light signals are detected by a light detector at the console unit and the signals are then digitized and transferred to a digital processing unit (for example the controller or a computer). Signal processing algorithms are then used to calculate phosphorescence lifetime. Lifetime information is then converted to pO2 value by application of the Stern-Volmer equation. The specific algorithm that is used depends on the source modulation pattern. For example, the light source can be amplitude modulated in a form of a square wave such that the source light is on for a period T1 and then off for a period T2. The phosphorescence signal is only detected while the source is off (for duration T2). A non-linear exponential fit procedure is then applied and the exponential time constant is evaluated and recorded. This time constant is then used as the phosphorescence lifetime in the Stern-Volmer equation to yield the pO2 value at the current sensing position along the sensing layer.

Resulting pO2 value is then displayed numerically or graphically on a monitor or printout. Graphical representation may be presented as a graph of partial pressure of oxygen versus tissue depth.

According to another example embodiment, the oxygen sensitive dye is mixed into a polymer matrix such as, but not limited to, cellulose acetate butyrate (CAB). Other polymer matrices may be selected on the basis of permeability to oxygen or other materials that are to be detected and other factors such as biocompatibility.

The polymer matrix may also incorporate a further dye or dyes mixed into the polymer matrix. The further dye may have a pH dependent fluorescence. In the case of this embodiment, the light source of the console emits radiation that excites the pH-sensitive dye to fluorescence and the oxygen-sensitive dye to phosphorescence and the detector receives both the phosphorescence and fluorescence radiation returned from the polymer matrix and the controller is programmed with algorithms that operate to evaluate both oxygen pO2 and pH level. Separation of the detector signal to a contribution of phosphorescence of the oxygen sensitive dye and a contribution of the fluorescence of the pH sensitive dye can be achieved by fitting the temporal decay of the signal to a multi-exponential function. The amplitude and lifetime of light emission from both luminescent dyes are deduced from computing the parameters that best fit the measured signal. The amplitudes or the lifetimes can then be used to separately evaluate the pO2 level and the pH level. A detailed description of simultaneous measurement of pO2 and pH is given in U.S. Pat. No. 4,923,819.

Similarly, the polymer matrix may include dyes sensitive to the presence of carbon dioxide ($CO_2$), calcium ion ($Ca^{++}$) and/or magnesium ion ($Mg^{++}$). In each of these, the light source emits radiation at a wavelength to excite the dye and the detector is structured to detect radiation returned from the dye by fluorescence or phosphorescence. The controller is configured with hardware or software to resolve signals from the detector to determine and display the concentration of the target substance which can then be determined as a function of depth or distance along the length of the sensing window.

Similarly, a temperature sensitive dye can be included in the polymer matrix to allow dual measurement of pO2 and temperature. A temperature sensitive dye can be for example Rhodamine B, in which the dependence of fluorescence on temperature has been investigated, D. Ross, M. Gaitan, and L. E. Locascio; "*Temperature Measurement in Microfluidic Systems Using a Temperature-Dependent Fluorescent Dye*"; *Anal. Chem.*, 73, 4117-4123 (2001).

According to another example embodiment, the light source of the console unit emits light to excite endogenic fluorophores such as, but not limited to, NADH (reduced form of nicotinamide adenine dinucleotide) in a wavelength that is transmitted through the oxygen-sensitive dye and to record fluorescence emission in wavelengths that are transmitted through the oxygen-sensitive dye. Here, for example NADH is excited at a wavelength of 340 nm and detected at a wavelength of 445 nm. PtOEP oxygen dye, for example, is transparent to both of these wavelengths.

DETAILED DESCRIPTION

Figure 1:
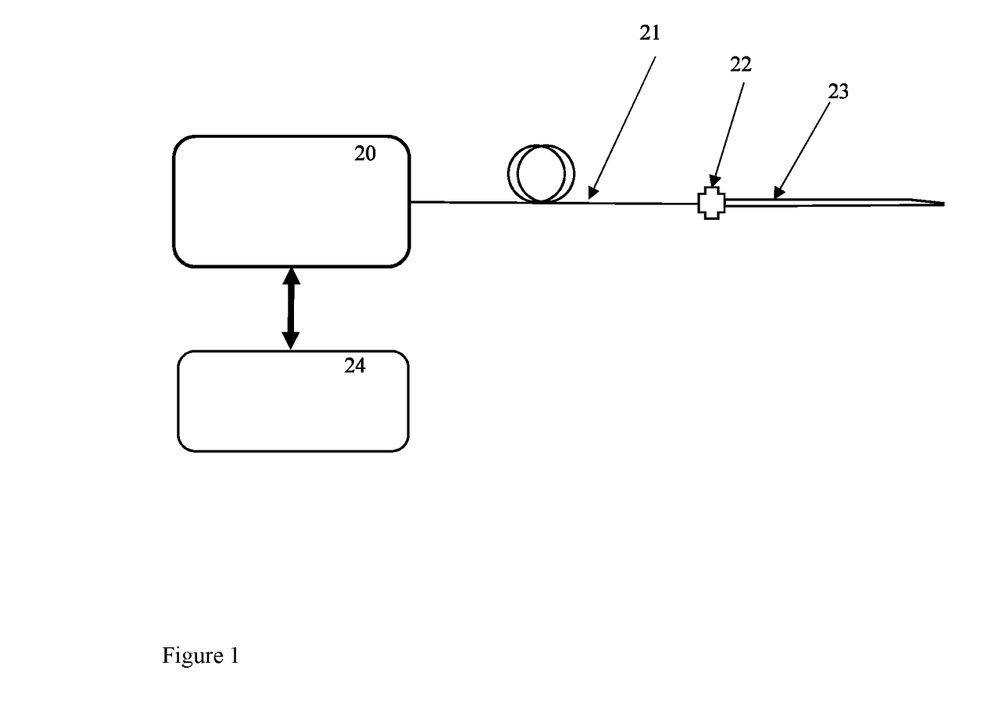
FIG. 1 is a schematic depiction of a depth scanning oxygen sensing system according to an example embodiment of the invention.
Figure 2:
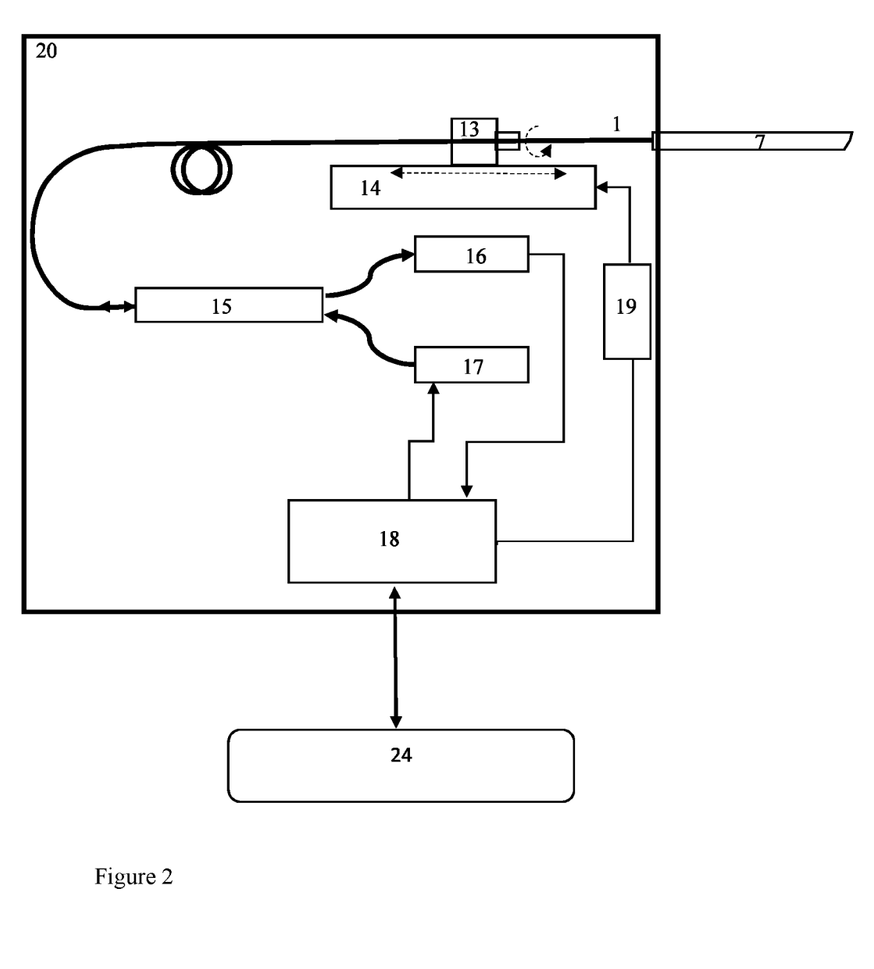
FIG. 2 is a schematic depiction of a console unit of a depth scanning oxygen sensing system according to an example embodiment of the invention.
Figure 3:
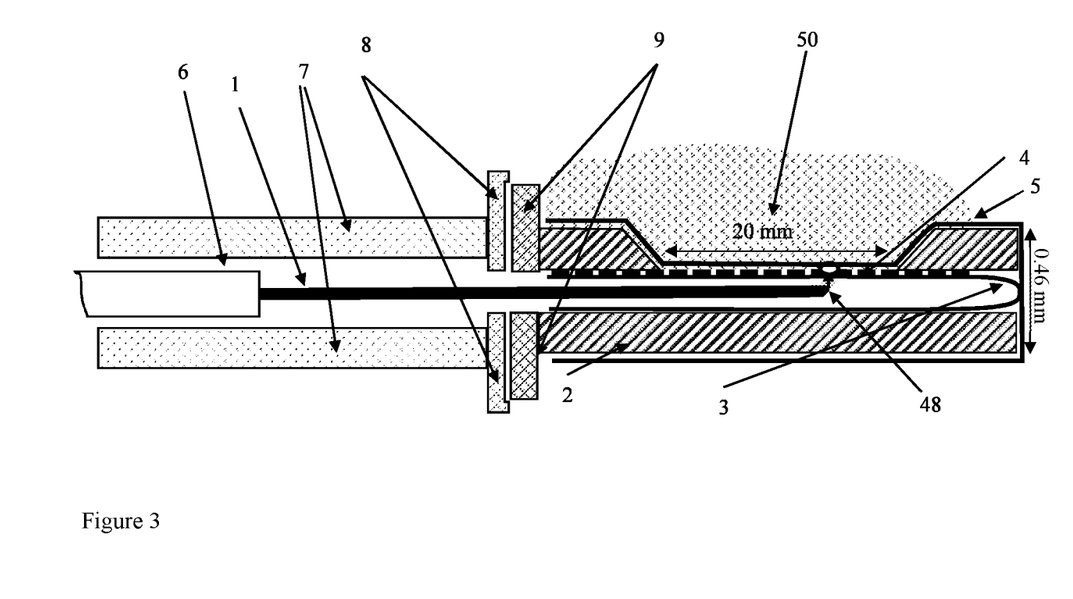
FIG. 3 is a schematic depiction of a needle oxygen probe according to an example embodiment of the invention.

Referring to FIGS. 1, 2, and 3, depth scanning oxygen sensing system generally includes base console 20 and needle sensor 23, connected by a single optical fiber assembly 21 and a connector 22. pO2 values are obtained by measuring phosphorescence lifetime of an oxygen-sensitive dye and using the Stern-Volmer equation relating excitation lifetime and pO2 in the micro-environment of the dye.

Referring particularly to FIG. 2, base console 20 generally includes excitation light source 17, light detector 16, fiber optic coupler 15, motorized translation stage 14, motorized rotation stage 13, motor driver unit 19, and a controller 18.

Excitation light source 17 emits an appropriate wavelength of light to excite a selected phosphorescent dye. Excitation light source 17 emits excitation light coupled into an optical fiber and connected to a fiberoptic coupler 15. The coupler directs part of the excitation light to optical fiber 1. Phosphorescence or fluorescence light is collected by the needle sensor 23 and propagates back in the optical fiber 1 and is coupled to the coupler 15. The phosphorescence or fluorescence light is directed by the coupler to the detector 16. A controller 18 (typically a digital microcontroller such as PIC18F24K40 manufactured by Microchip Inc.) is used to control the output power of the excitation light source 17 and to record the electronic signals of the light detector 16. The controller is also used to control the motorized translation stage and the motorized rotation stage by sending appropriate electronic signals to the motor driver unit 19. The motor driver 19 supply appropriate electrical current signals to the motors in the translation stage 14 and the rotation stage 13 causing the fiber 1 to translate and rotate such that its distal tip inside the needle sensor 23 is positioned appropriately to emit and collect light to and from a desired position along the sensitive dye-doped layer 4. The controller is also equipped with a bidirectional data channel to a user interface device 24 (such as a computer) allowing the user to operate the scanner.

Translation stage 14 supports the rotation stage 13 which in turn supports the optical fiber 1. Operating the translation stage causes optical fiber 1 to move along a straight line path without rotating optical fiber 1. Operating the rotation stage 13 causes the optical fiber 1 to rotate.

Controller 18 is operably coupled to input/output terminal 24, motors driver unit 19, light detector 16 and excitation light source 17. Controller 18 is programmed with appropriate algorithms to control excitation light source 17 and to receive and process information from light detector 16 and to control motors driver unit 19 which in turn controls motorized scanning device 14 and rotation stage 13.

Input/output terminal 24 is coupled to controller 18 and presents, for example, a graphical user interface by which an operator can input and receive information related to base console 20 and needle sensor 23. The controller 18 records and analyze digital signals acquired from the light detector 16 and then sends the processed signals to the user interface unit 24 for further processing and display.

Base console 20 is operably coupled to needle sensor 23 at least by optical fiber assembly 21 which includes an optical fiber 1, tight coating 6, and loose sleeve 7 (details shown in FIG. 3).

Referring particularly to FIG. 3, needle sensor 23 generally includes optical fiber 1, capillary glass tube 3, syringe needle 2, fiber sleeve 7, dye doped polymer layer 4 and thin protection layer 5. Optical fiber 1 is housed within capillary glass tube 3 which is, in turn, housed within syringe needle 2. Optical fiber 1 terminates at angled end 48. Angled end 48 is angled appropriately to cause total internal refraction of both excitation light and phosphorescence or fluorescence light. In an example embodiment, angled end 48 is terminated and polished at an angle of 45 degrees. The angled end 48 delivers excitation light to an oxygen sensing layer composed of a thin layer of dye-doped polymer layer 4. The dye-doped polymer layer 4 is coated on the outer wall of a sealed capillary glass tube 3. Phosphorescence light is generated in the sensing layer 4. Part of the phosphorescence emission is collected by the angled fiber end 48 and delivered to the detection section by the optical fiber 1. The glass capillary is housed in a stainless steel syringe needle 2 that has a side-window allowing physical contact between the sensing layer and the tissue. The optical fiber can be translated horizontally with respect to the static fiber sleeve 7 and the glass capillary 3 by pulling or pushing the back end of the fiber by the translation stage in unit 20 (shown in FIG. 2). This allows for optical probing of any point at the sensing layer and within the side opening in the needle shaft 2. The fiber 1 may have a tight coating 6 to enhance its mechanical properties allowing for better force and torque transmission from the translation and rotation stage in unit 20 to the front angled end of the fiber 48. In this case parts 1 and 6 are in tight contact such that they move together. A connector 22 composed of two parts (8 and 9) allows disconnecting the needle assembly (parts 2, 3, 4, 5, and 9) from the fiber assembly (parts 1, 6, 7, and 8) once the fiber assembly is completely retracted and positioned in the sleeve 7. This feature allows exchanging the needle unit for sterilization or replacement. A thin protection layer of oxygen-permeable layer 5 is deposited by dip coating to prevent degradation of the sensing layer. In addition to translation the fiber can also be rotated by rotating the back end of the fiber. Rotation is necessary for aligning the fiber illumination and receiving direction with the side window in the needle 2.

Syringe needle 2 may be formed, for example, of stainless steel or another rigid biocompatible material and is perforated by sensing window 50. According to an example embodiment, sensing window 50 may be approximately twenty mm long, though sensing window 50 may be longer or shorter as desired or necessary. Syringe needle 2 according to an example embodiment may have an outside diameter of 0.46 plus or minus 0.02 mm though size can vary.

Dye doped polymer layer 4 overlies capillary glass tube 3 at least in the vicinity of sensing window 50. Thin protection layer 5 in turn covers dye doped polymer layer 4. Thin protection layer 5 is oxygen permeable and may be applied, for example, by dip coating to prevent degradation of dye doped polymer layer 4.

Sensing window 50 is structured to allow physical contact between thin protection layer 5 and surrounding tissue into which needle sensor 23 is inserted. Thus, dye doped polymer layer 4 (or protection layer 5 if it is applied) is in direct oxygen sensing contact with surrounding tissue into which needle sensor 23 is inserted.

Optical fiber 1 is positioned within capillary glass tube 3 so that angled end 48 is directed toward sensing window 50 (light emitted from the fiber tip is directed toward the sensing window 50).

Oxygen Transduction

Oxygen sensitive dye in dye doped polymer layer 4 is excited by an optical pulse emitted from angled end 48. In case of a dye of high quantum yield for inter-system crossing, a significant part of the dye molecules will be excited to the first triplet state. The dynamics of the relaxation back to the ground state depends on oxygen concentration. The decay is exponential having a lifetime $t_1$. The lifetime $t_1$ depends on oxygen partial pressure according to Stern-Volmer equation, H. Boaz and G. K. Rollefson, "*The Quenching of Fluorescence. Deviations from the Stern-Volmer Law,*" *J. Am. Chem. Soc.* 72(8), p. 3435-3443 (1950), as follows:

$$\frac{I_0}{I_1} = \frac{t_0}{t_1} = 1 + k_{O2} + t_0 p \qquad (1)$$

where $I_0$ and $I_1$ is mean phosphorescence intensity in zero oxygen and at oxygen partial pressure of p respectively, $t_0$ is the lifetime at zero oxygen conditions, $t_1$ is the lifetime at p partial oxygen pressure, and $k_{O2}$ is the quenching rate coefficient.

Following optical excitation of a photosensitizer dye, phosphorescence intensity decays exponentially. This decay can be described by the following expression.

$$I(t) = I_{PH} \exp(-t/t_1) \qquad (2)$$

where $I_{PH}$ is the initial phosphorescence intensity immediately after excitation illumination stops. By measuring the temporal decay of the phosphorescence (I(t)), and fitting the measured data points at a set of discrete time intervals to an exponential function, the lifetime ($t_1$) can be extracted. Equation 1 is then used to evaluate the oxygen partial pressure.

Error Analysis: The dominant source for systematic measurement error is attributed to the dependence of phosphorescence lifetime on temperature. Coyle and Gouterman in L. M. Coyle, and M. Gouterman, "*Correcting lifetime measurements for temperature*", *Sensors and Actuators B* 61, p. 92-99 (1999), have measured the temperature dependence of phosphorescence lifetime in platinum meso-tetra (pentafluorphenyl) porphyrin (Pt-TFPP). They have found that lifetime decreases at a rate of 0.3%/° C. in the temperature range of 10-50° C. Similar temperature dependence of phosphorescence lifetime has been measured by Zelelow et. al. in B. Zelelow, G. E. Khalil, G. Phelan, B. Carlson, M. Gouterman, J. B. Callis, and L. R. Dalton "*Dual luminophor pressure sensitive paint: II. Lifetime based measurement of pressure and temperature.*" *Sensors and Actuators B: Chemical* 96.1, p. 304-314 (2003) for platinum-tetra(pentafluorophenyl) porpholactone (Pt-TFPL). In a typical application of a device described here, the oxygen probe will be inserted in a living tissue (animal or human) where temperature range is within the range of 32° C. to 42° C. If the tissue temperature is not measured, this uncertainty will lead to a systematic error of up to 3% in pO2 estimation.

Example Device Embodiment Configuration

Optical fiber 1 may be a multimode, having a 105 μm core size, 125 μm cladding size and 250 μm jacket size, and a numerical aperture (NA) of 0.22. To form angled end 48 a distal end of the fiber can be terminated by 45 degree polishing.

Excitation light source 17 can be a Nd:YAG CW frequency doubled laser, 532 nm, 200 mW, Square wave modulated. Light detector 16 can be a detector: Avalanche Photodiode integrated with a transimpedance amplifier (100 kOhm).

An example oxygen sensitive dye can be PtOEP.

A polymer matrix for dye doped polymer layer 4 and thin protection layer 5 can be formed of cellulose butyrate (CAB).

Syringe needle 2 can be formed from a syringe needle gauge 26, length 1.5".

Capillary glass tube 3 can have an inside diameter of 0.15 and an outside diameter of 0.25 mm.

Information related to partial pressure of oxygen may be presented as absolute values as a function of depth or distance along sensing window 50 within the tissue or as relative values.

According to another example embodiment, the oxygen sensitive dye is mixed into a polymer matrix such as, but not limited to, cellulose acetate butyrate (CAB). Other polymer matrices may be selected on the basis of permeability to oxygen or other materials that are to be detected and other factors such as biocompatibility.

The polymer matrix may also incorporate a further dye or dyes mixed into the polymer matrix or otherwise on the exterior of capillary glass tube 3. The further dye may have a pH dependent fluorescence. In the case of this embodiment, excitation light source 17 emits radiation at one or several wavelengths that excites the pH-sensitive dye to fluorescence and the oxygen-sensitive dye to phosphorescence and the detector receives both the phosphorescence and fluorescence radiation returned from the polymer matrix and the controller is programmed with algorithms that operate to evaluate both oxygen pO2 and pH level.

Similarly, the polymer matrix may include dyes sensitive to the presence of carbon dioxide ($CO_2$), calcium ion ($Ca^{++}$) and/or magnesium ion ($Mg^{++}$). In each of these, the light source emits radiation at a wavelength appropriate to excite the dye and the detector is structured to detect radiation returned from the dye by fluorescence or phosphorescence. Controller 18 is configured with hardware or software to resolve signals from light detector 16 to determine and display a concentration of the target substance which can then be determined as a function of depth or distance along the length of sensing window 50.

Similarly, the polymer matrix may also incorporate a further dye or dyes mixed into the polymer matrix or otherwise on the exterior of capillary glass tube 3. The further dye may have a temperature dependent fluorescence. In the case of this embodiment, excitation light source 17 emits radiation at one or several wavelengths that excites the temperature-sensitive dye to fluorescence and the oxygen-sensitive dye to phosphorescence and the detector receives both the phosphorescence and fluorescence radiation returned from the polymer matrix and the controller is programmed with algorithms that operate to evaluate both oxygen pO2 and temperature.

According to another example embodiment, excitation light source 17 emits light to excite endogenic fluorophores such as, but not limited to, NADH at a wavelength that is transmissible through the oxygen-sensitive dye and to record fluorescence emission in wavelengths that are transmissible through the oxygen-sensitive dye. Here, for example, NADH is excited at a wavelength of 340 nm and detected at a wavelength of 445 nm. PtOEP oxygen dye, for example, is transparent to both of these wavelengths.

Accordingly, the invention also includes a method of determining tissue oxygen level over a linear distance and presenting tissue oxygen level graphically or numerically and in absolute values or relative values.

An example method, includes inserting a needle sensor 23 into a tissue to be evaluated as to oxygen level so that a sensing window 50 having a dye doped polymer layer 4 is in close apposition to the tissue; translating the angled end 48 of an optical fiber 1 inside of the dye doped polymer layer 4 to illuminate the dye doped polymer layer 4 with excitation radiation and to receive phosphorescence radiation from the dye doped polymer layer 4; receiving the phosphorescence radiation at a light detector 16; sending signals from the light detector 16 to a controller and processing the signals using the Stern-Volmer equation relating excitation lifetime and pO2 in the micro-environment of the dye.

In operation, needle sensor 23 is inserted into a tissue, the partial pressure oxygen profile of which is desired to be determined. The tissue makes contact with thin protection layer 5 and dye doped polymer layer 4 via sensing window 50 in syringe needle 2. Oxygen molecules can diffuse through thin protection layer 5 to dye doped polymer layer 4 to physically interact with dye molecules in layer 4.

Excitation light source 17 is activated to emit excitation light which travels via optical fiber 1 to illuminate dye doped polymer layer 4. Phosphorescence light emitted by dye doped polymer layer 4 is received by angled end 48 of optical fiber 1 and returned via optical fiber 1 to light detector 16. Actuator 19 may be actuated to operate translation stage 14 which scans optical fiber 1 longitudinally thus causing angled end 48 to move within capillary glass tube 3. As angled end 48 moves relative to dye doped polymer layer 4, accordingly, partial pressure of oxygen within the tissue may be sensed along a linear depth as long as sensing window 50.

What is claimed is:

1. An oxygen scanning device, comprising:
   a console unit, the console unit including a light source emitting excitation radiation, a controller, and a detector configured to receive and detect phosphorescence radiation;
   a needle sensor operably, optically coupled to the console unit by an optical fiber received within a transparent tube housing the optical fiber, the transparent tube being coated by an oxygen-sensitive dye material on an outer side thereof, wherein said needle sensor is constructed and arranged for insertion into, and be positioned at a stationary location, relative to a lumen, and said optical fiber is movable relative to said lumen within said transparent tube, and further wherein said needle sensor has an interior and a window opening into said interior, wherein a portion of said transparent tube is adjacent to and traverses said window opening within said interior;
   the optical fiber being terminated by an angled reflector at a distal end thereof wherein excitation radiation is directed to the oxygen-sensitive dye material via the optical fiber and phosphorescence radiation from the oxygen-sensitive dye material is returned via the optical fiber from the oxygen-sensitive dye material to the detector, the detector generating a signal responsive thereto; and
   a motor operatively engaged to said optical fiber and in communication with said controller, said motor, responsive to said controller, providing at least one of a translational stage and a rotational stage moving said optical fiber within said transparent tube, wherein said controller determines partial pressure of oxygen based on the detector signal.

2. The oxygen scanning device of claim 1, in which the oxygen-sensitive dye material is a dye embedded in a polymer matrix.

3. The oxygen scanning device of claim 2, further comprising a second dye mixed into the polymer matrix, the second dye having pH dependent fluorescence.

4. The oxygen scanning device of claim 3, the second dye having fluorescence or phosphorescence dependent on the presence of a target substance selected from the group consisting of carbon dioxide, calcium ion and magnesium ion.

5. The oxygen scanning device of claim 2, wherein the light source of the console emits radiation that excites a second dye and the oxygen-sensitive dye material and the detector receives the phosphorescence radiation returned from the polymer matrix and fluorescence radiation from the second dye, said controller programmed with an algorithm that evaluates pH level.

6. The oxygen scanning device of claim 2, further comprising a second dye mixed into the polymer matrix, the second dye having temperature dependent fluorescence.

7. The oxygen scanning device of claim 6, wherein the light source of the console emits radiation that excites the second dye and the oxygen-sensitive dye material and the detector receives the phosphorescence radiation and fluorescence radiation returned from the polymer matrix and said controller is programmed with an algorithm that evaluates temperature.

8. The oxygen scanning device of claim 6, wherein the light source emits excitation radiation at a wavelength of 340 nm and the detector detects fluorescence radiation at a wavelength of 445 nm.

9. The oxygen scanning device of claim 1, wherein the oxygen-sensitive dye material is coated by a protection layer of an oxygen-permeable material.

10. The oxygen scanning device of claim 1, wherein the transparent tube is housed in a needle.

11. The oxygen scanning device of claim 1, wherein light source emits radiation that excites endogenic fluorophores at a first wavelength that is transmissible through the oxygen-sensitive dye material and the detector detects light returned from fluorescence emission by the endogenic fluorophores at a second wavelength that is transmissible through the oxygen-sensitive dye material.

12. The oxygen scanning device of claim 11, wherein the endogenic fluorophores comprise a reduced form of nicotinamide adenine dinucleotide.

13. The oxygen scanning device of claim 1, wherein said optical fiber is a single optical fiber.

* * * * *